United States Patent
Moghaddam et al.

(10) Patent No.: US 7,318,671 B1
(45) Date of Patent: Jan. 15, 2008

(54) HEAT-FLUX BASED EMISSIVITY/ABSORPTIVITY MEASUREMENT

(75) Inventors: Saeed Moghaddam, Columbia, MD (US); John Lawler, Potomac, MD (US); Jungho Kim, College Park, MD (US)

(73) Assignee: Atec, Inc., College Park, MD (US)

( * ) Notice: Subject to any disclaimer, the term of this patent is extended or adjusted under 35 U.S.C. 154(b) by 97 days.

(21) Appl. No.: 11/231,453

(22) Filed: Sep. 21, 2005

Related U.S. Application Data

(60) Provisional application No. 60/612,365, filed on Sep. 23, 2004.

(51) Int. Cl.
*G01N 25/00* (2006.01)
(52) U.S. Cl. .............................................. 374/9; 374/30
(58) Field of Classification Search .................... 374/9, 374/30
See application file for complete search history.

(56) References Cited

U.S. PATENT DOCUMENTS 4,117,712 A * 10/1978 Hager, Jr. ..................... 374/9

OTHER PUBLICATIONS

RdF HF S-LII Heat Flux Sensors; 3 Pages.

* cited by examiner

*Primary Examiner*—Gail Verbitsky
*Assistant Examiner*—Megann E Vaughn
(74) *Attorney, Agent, or Firm*—Rosenberg, Klein & Lee

(57) ABSTRACT

A mechanism and method for directly observing data from which the thermal emissivity or absorptivity of a surface can be calculated. The invention teaches the use of a substantially planar heat-flux or heat-flow sensor employing a thermopile, to measure the rate of heat dissipation from a radiating surface thermally attached to one side of the heat-flux sensor where the radiating surface is exposed to a first temperature and where the second side of the heat flux sensor is in thermal contact with a heat source at a second higher temperature.

12 Claims, 3 Drawing Sheets

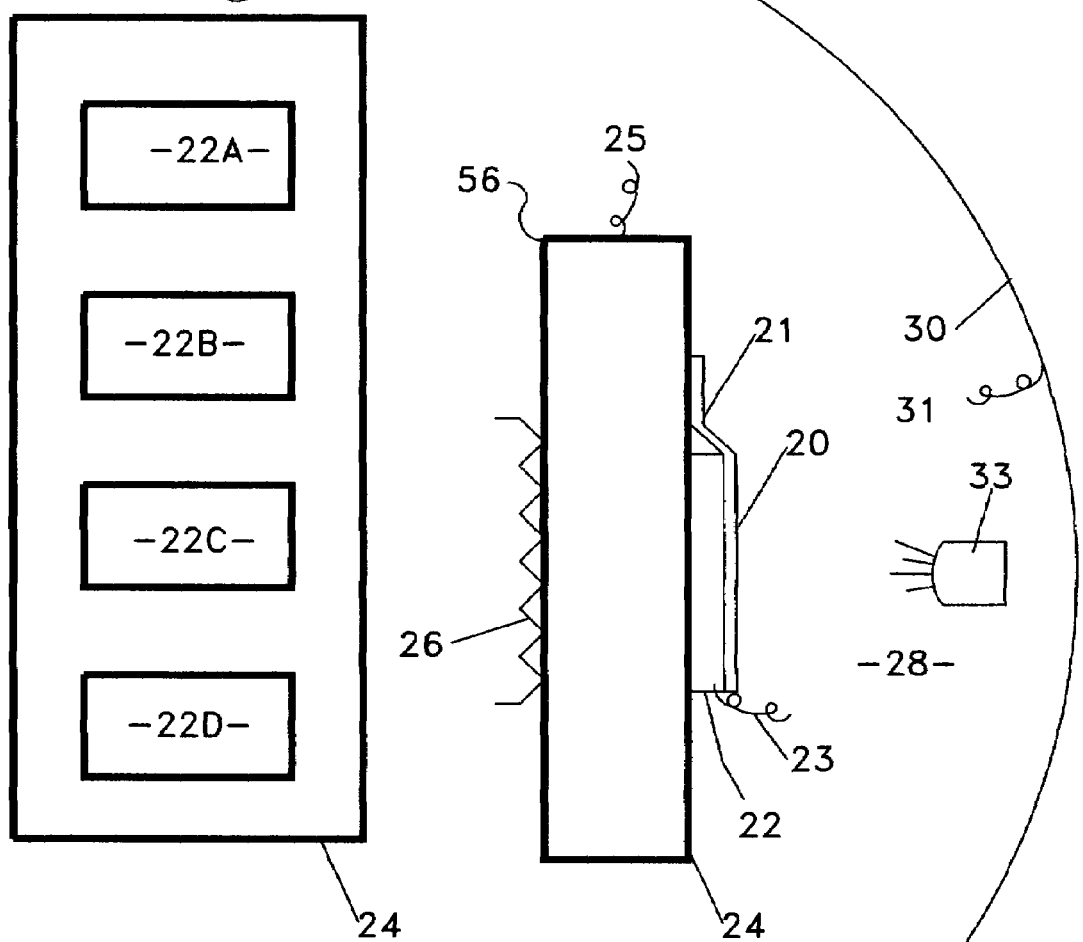
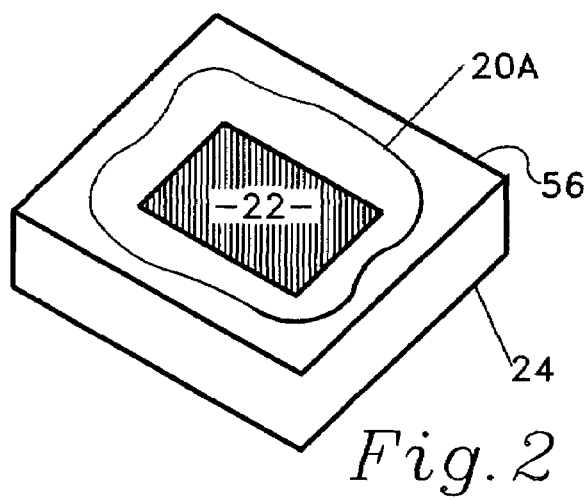

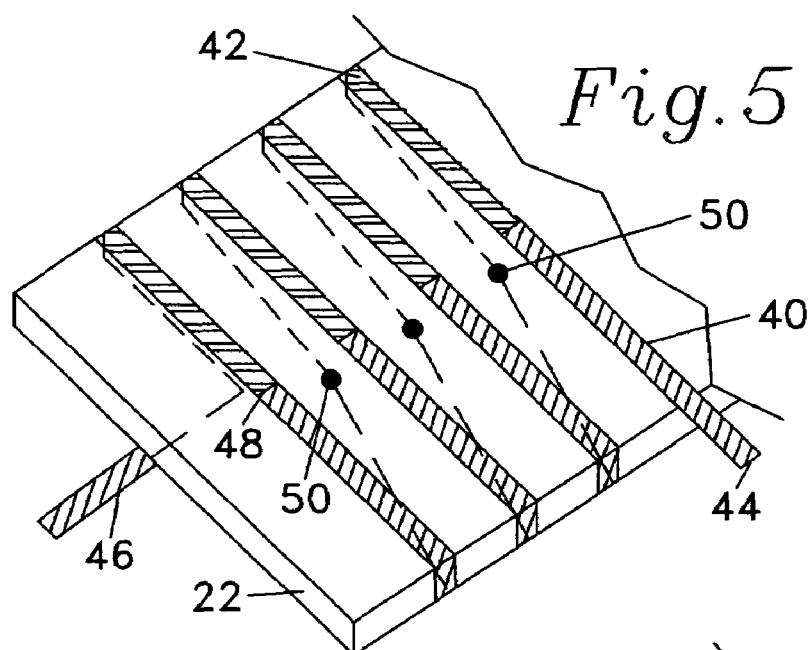
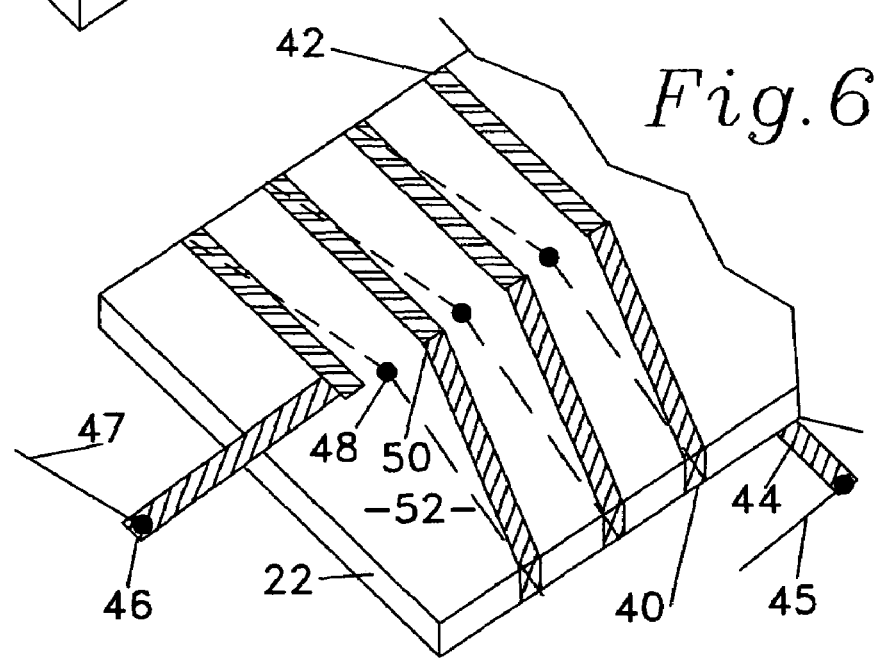

HEAT-FLUX BASED EMISSIVITY/ABSORPTIVITY MEASUREMENT

PRIORITY

This Non-Provisional patent application claims priority based on a Provisional Patent Application filed 23 Sep. 2004 (09-23-2004) having Ser. No. 60/612,365 having the same inventors and substantially the same title.

STATEMENT REGARDING FEDERALLY SPONSORED OR-FUNDED RESEARCH

This invention was made with Government Support under Contract FA8650-04-M-5020 awarded as an Air Force SBIR Phase I Project.

The Government has certain rights in the invention.

BACKGROUND OF THE INVENTION

1. Field of the Invention

This invention relates to improved apparatus and method for measuring the thermal emissivities of surfaces and coatings.

2. Background of the Art

To simplify the following discussion the term heat loss and the term emissivity are used and the object or surface under discussion is considered to be at a higher temperature than its environment. However, it should be noted that an object can gain or lose heat by conduction and convection to a vapor or gas and can gain or lose heat by radiation. Therefore the principles that apply that allow an object or surface to be cooled or to dissipate heat when the environment is at a lower temperature than the object or its environment also apply to cause an object or surface to be warmed when the environment is at a higher temperature than the object or surface.

When warmer objects are placed in colder environments and must be kept warm, enough heat must be supplied to the object to offset any heat loss to the colder environment. In a gaseous environment, like that on earth's surface, heat can be lost from the object or gained by conduction and convection to the surrounding gas and by radiation. Heat loss by convection and convection can only occur at substantial rates in such a gaseous environment. Since in outer space there is not significant concentration of gases that could effect heat loss from the object, knowledge of the expected amount of heat loss from radiation would affect the amount of heat or energy that must be planned to be supplied to the object to keep it adequately warm. Radiative heat loss from an object occurs at the object's surface. The amount of heat leaving the object's surface depends on the temperature difference between the object and the place receiving the radiation and a surface characteristic. This surface characteristic is called Emissivity. Similarly, direct radiation from the sun could add to possible internal heat loads demanding cooling. The surface characteristic that affects the rate at which a surface absorbs energy radiated to it is called Absorptivity. In deep space the so-called heat sink temperature (the place receiving the heat) is in the range of 2.5 to 3.0 K on the absolute Kelvin scale.

Knowledge of the emissivity and absorptivity of the exposed surface of anything sent into space is an important requirement since these provide an accurate measure of the amount of heat that must be provided within to balance that lost by radiation. Large panels having high emissivity surfaces are used to dissipate heat that has been generated inside or absorbed by external surface of a space craft.

Emissivity is a measure of the rate at which a surface at one temperature radiates heat to another surface or body at a lower temperature. Absorptivity is like Emissivity except it is a measure of the rate at which a surface at one temperature absorbs heat from a surface or body at a higher temperature. Emissivity is expressed as a dimensionless number between 0 and 1 defined as the ratio of energy emitted from the object's surface to the energy emitted from the surface of a blackbody or perfect emitter at the same conditions. Spectral Emissivity is a special case directed to the emissivity of a surface at a given spectral color or wavelength.

PRIOR ART

The calculation or measurement of emissivity of a surface requires knowledge of three variables: The temperature of the surface, the temperature of the sink to which heat is being radiated by the surface and the amount of heat being radiated by the surface. The temperature of the surface is most frequently measured with a thermometer or thermocouple thermally attached to the surface or attached to the structure on which the emitting surface is located, for instance the outer skin of a satellite. Measurement of the amount of radiated heat is more difficult. In laboratories calorimeter arrangements are employed where a body of water, for instance, is circulated through tubes attached to the inside of the emitting surface and the temperature change and flow rate of the water are measured. More recently, laboratory techniques for measuring emissivity teach the use of a flat band of an electrical resistance material such as a Nickel-Chromium alloy that is coated with the material whose emissivity is to be tested. Electricity is passed through the band, thereby heating it. A measurement of the current and voltage drop across the test section provides an accurate measure of the heat radiated and a temperature measurement of the band provides the source temperature from which emissivity can be calculated. This and other related information are found at: (http://www.npl.co.uk/thermal/stuff/guide4.html) However, this emissivity measurement system can only be used in the laboratory or under special conditions and it cannot be employed to measure absorptivity.

The heat-flux sensor employed in the invention is a commercial device made by Rdf Corp., there are other manufacturers offering similar devices. There is no literature known to the inventors that teaches the use of such devices for observation of data from which emissivity or absorptivity can be calculated.

SUMMARY OF THE INVENTION

The invention teaches the use of a heat-flux or heat-flow meter for measuring data from which surface emissivity or absorptivity can be calculated. The heat flux meter comprises a system for accurately measuring the temperature difference between the two sides of a thermal barrier having a known thermal resistance. One side of the heat-flux meter is thermally attached to a heat source having a first temperature. The radiating surface is thermally attached to the other side of the heat-flux meter and exposed to a second temperature lower than the first temperature whereby knowledge of the first and second temperatures and the heat flow through the heat-flux meter provides the required data for calculation of emissivity of the surface.

OBJECTS AND ADVANTAGES a) It is an object of this invention to provide a mechanism for accurate measurement of data from which emissivity or absorptivity characteristic of a surface can be calculated.

b) It is a further object to provide such a mechanism that provides direct measurement of the heat flow to or from the emitting/absorbing surface.

c) It is a further objective of the mechanism to apply a heat-flux sensor in substantial thermal contact with the radiating/absorbing surface.

d) It is a further object to provide such a mechanism for providing a sequence of such data over varying conditions.

e) It is a further object to provide a mechanism that will allow substantially simultaneous data observations at substantially identical conditions for several surfaces having different emissivities.

f) It is a further object to provide a mechanism that does not require the measurement or knowledge of heat input.

g) It is a further object to provide such a mechanism that does not require effective thermal insulation of the heat radiating body from its surroundings.

h) It is a further object to provide such a mechanism that inherently has low thermal mass and high scalability thereby allowing effective data observation with respect to variable emissivity/absorptivity surfaces.

i) It is a further object to provide such a mechanism that inherently has low thermal mass and high scalability thereby providing good temporal resolution and allowing effective data observation under transient conditions.

j) It is a further object to provide a mechanism that allows a sequence of data to be taken that allows emissivity of the test surface to be calculated over a sequence of conditions.

k) It is a further object to provide such a mechanism that does not rely on a temperature history of the surface or the mechanism.

l) It is a further object to provide such a mechanism that provides accurate data for emissivity calculation, even during changing source and sink temperatures.

m) It is a further object to provide such a mechanism that can measure the emissivities of a surface having changeable emissivities.

n) It is a further object to provide such a mechanism that has low mass thereby allowing it to respond rapidly to changing condition.

Other objects and advantages will become apparent as expressly disclosed or implied in the following detailed description of the various embodiments of the invention.

BRIEF DESCRIPTION OF THE DRAWINGS

FIG. 1 shows an assembly of the invention positioned to emit or absorb radiation in a hemisphere having a horizontal axis.

FIG. 2 is an isometric view of the assembly of FIG. 1.

FIG. 3 is a planar view of an extended heat source 24 on which four individual heat-flux sensors are positioned.

FIGS. 5 and 6 show top and bottom views of one embodiment of a heat-flow sensor.

DETAILED DESCRIPTION OF THE PREFERRED EMBODIMENTS

Figure 4:
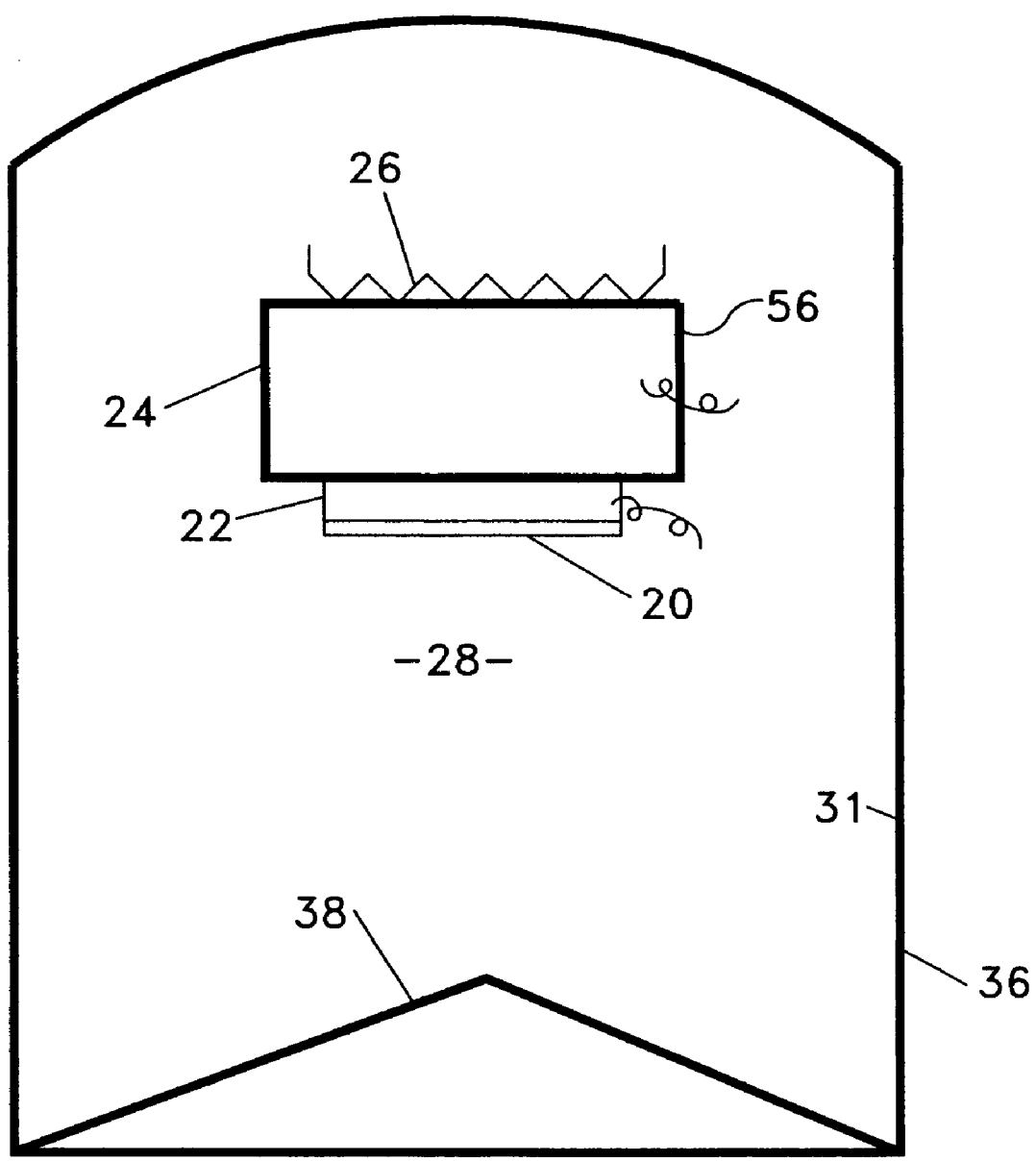
FIG. 4 displays the assembly of FIG. 1 positioned to emit or absorb radiation in a hemisphere having a substantially vertical axis and positioned within a sealed pressure controlled chamber.

In the following description the surface 20 is substantially always described as an emitting surface. However, the heat-flux sensor can indicate and measure heat flow in either direction; 1) from the heat source 24, whose temperature is dropping, through the heat-flux sensor 22 and the emitting surface 20 to an external heat sink or, 2) in contrast, from an external source of radiant energy 33 to surface 20, now an absorbing surface, through heat-flux sensor 22 to heat sink 24 whose temperature is now rising. It must be noted that surfaces are being developed that have an externally controllable emissivity. Such a surface is described in a paper titled, "Electrostatic Switchable Applique" by Biter, Hess and Oh, (CP746 Space Technology and Applications International Forum, STAIF 2005) and is or will be used for temperature control in spacecraft. Such emissivity-controllable surfaces are called 'Active' surfaces. The invention disclosed herein is unusually applicable to real-time observation of the varying emissivities of such surfaces.

In FIG. 1 there is shown a side view of an assembly of the invention where data from which emissivity of surface 20 is to be observed. Heat-flux sensor 22 is positioned between a heat source 24 and emitting surface 20. Heat-flux sensor 22 is thermally fastened to heat source 24. The fastening means may be a contact cement or simply a thermally conductive grease. When applied in a high-vacuum environment grease may outgas so a cement such as Tra-Con's Tra-Bond 2151, a thixotropic heat-conductive epoxy system with low outgassing qualities should be employed. Tra-Con is located in Bedford Mass. Heat flux-sensor 22 and emitting surface 20 are shown having substantial thicknesses. However, no inference is to be drawn about their actual thickness. However, one of the characteristics of the heat flux sensors that makes them highly suitable for use under transient conditions is their very low mass and relatively high thermal conductance. The unit employed exhibited a very low thermal capacitance of 0.02 Btu/sq.ft-deg. F., a thermal impedance of 0.01 deg. F./(Btu/(sq.ft.-hr)). These qualities allow rapid responses and minimum temperature drop across the sensor itself. In one commercial version of the heat-flux sensor manufactured by RdF Corp. Surface, the sensor is 0.47×1.8 inches and is 0.0065 inches thick. RdF corporation is located at 23 Elm Avenue, PO Box 490 Hudson, N.H. 03051-0490.

Surface 20 may be a coat of paint, a film of some thin material as by vacuum deposition, a piece of metal with or without a surface finish, etc. The only requirements imposed on the surface 20 are that it fully cover sensor 22 and that it be in close thermal or heat transfer contact with sensor 22. While the emitting surface 20 may extend over and beyond the surface of sensor 22 the extended portions must be in direct contact 21 with the heat source/sink 24. This is because heat flowing from sink 24 to surface 20 does not traverse heat-flux sensor 22 and therefore does not affect the data pertinent to emissivity calculation. However, if the surface 20 extending beyond heat-flux sensor 22 is not in direct contact with heat source/sink 24, heat absorbed/emitted by the extended surface 20 may flow to the sensor 22 thereby augmenting the heat flow directly related to the surface 20 immediately in contact with sensor 22, thereby providing incorrect results.

The assembly 56 of FIG. 1 is positioned in an environment 28 that is preferably a gas at ultra-low pressure. In space or earth orbit applications the pressure may be close to absolute zero. Under these conditions the opportunity for convective or conductive heat transmission from the surface 20 to the surrounding gas is low to zero. Such conditions can be secured in the laboratory by evacuation to pressures in the region of 3E-11 bar. However, at higher pressures, correction for heat transmission from surface 20 by convection or conduction will probably have to be performed, especially when measuring data from which to calculate emissivity of surfaces expected to exhibit low emissivities. (Relationships for estimating such heat transfer can be found in ASHRAE Handbook of Fundamentals 2005, Chapter 3 pages 16-18 and sources such as chemical and mechanical engineering handbooks, however, quantitative calibration for such gaseous convection and conduction may have to be performed to secure the required accuracy, especially where emissivity to be observed is low.)

The temperature of heat sink 30 can be measured by a sensor having leads 31. The leads 25 and 31 will be employed as a reference for the respective temperatures of source 24 and sink 30. The surface of sink 30 acts more effectively as a heat sink or absorber of radiant energy if it is coated with a material such as carbon black. However, deep space environment is considered such a condition.

Typically heat source 24 is a copper block having dimensions greater than the single or multiple (see FIG. 3) heat-flux sensors 22, 22A etc, to be mounted thereon. In one series of tests, block 24 had a thickness of 0.25 inches. Under test conditions it is desirable that heat source 24 exhibit high thermal conductivity to minimize temperature gradients across the heat sink. Therefore aluminum, silver or similar materials would be suitable. Under practical conditions in space orbit, however, heat sink 24 may be the environmental gas which the astronauts breath, the heat-flux sensor 22 being attached to the radiating or absorbing surface 20 that is also the outer metallic shell of the space-craft. Temperature measuring devices having leads 25 are positioned on or embedded in source/sink 24. Typically, the temperature measuring devices are thermocouples. Type-T (copper-Constantan) and Type-K (Chromel-Alumel) are common types. Their outputs are measured with instruments that accurately measure DC voltages in the millivolt range. A reference temperature must be provided as by an ice bath. However, modern instrumentation provides an automatic internal reference. An example of such an instrument is the Agilent 34970A indicator-recorder. While thermocouples have been widely employed for temperature measurement, such devices as RTDs (resistance temperature devices) whose electrical resistance changes predictably with temperature are widely employed for these purposes. Block 24 is described as a heat source when it is placed warm in a cold environment since it imparts an observable but gradually dropping temperature to the heat-flux sensor 22 thereby providing a gradually changing temperature difference across the emitting surface 20. Heater 26 may be provided for the purpose of stabilizing the temperature of heat source 24 when required. The use of a heat source 24 having greater mass encourages stable measurements since the heat dissipated or absorbed allows the larger mass to change temperature more slowly. However, heat sources/sinks of low mass such as the outer skin of a space-craft can be employed as sources/sinks 24 so long as it is understood that their temperatures may change rapidly. In FIG. 1 radiant heat source 33 allows direct measurement of surface absorptivity.

FIG. 2 illustrates the assembly 56 of FIG. 1 in an isometric view. There, the emitting surface 20A extends substantially beyond the surface of heat-flux sensor 22 but is in thermal contact with heat source 24 throughout. Therefore, there is no thermal incentive for heat received in the peripheral area fo flow to the heat-flux sensor 22.

In FIG. 3 there is shown an enlarged heat source 24 on the surface of which are mounted four heat-flux sensors, 22A-22D. These are all exposed to the same environment and have substantially identical source temperatures 25 and sink temperatures 31. The emitting surfaces covering the heat-flux sensors 22A, 22B etc. can be the same or different. Employing the same emitting surface for several heat-flux sensors allows a statistical measure of a more highly confident value for the emissivity. If each heat-flux sensor is provided with a different emitting surface, a rapid determination of significant differences in emissivity can be observed immediately.

In FIG. 4 there is shown a vacuum tight enclosure 36 providing an environment 28. Typically the enclosure 36 is part of a Dewar vessel that is filled with a volatile coolant, thereby establishing a fixed wall temperature. To simulate outer space conditions it is common to employ liquid nitrogen that boils at about −196 C or 77 K at atmospheric pressure as a cold sink. To improve the absorptivity of the inner surface of vessel 36, it is frequently coated with carbon black in some form. Cone 38 is provided to reduce heat radiated from surface 20 and assembly 56 from being reflected back to surface 20.

In FIGS. 5 and 6 the alternate sides of heat-flux sensor 22 are displayed in a rudimentary form for illustration. Heat-flux sensor 22, in its most common construction is formed of a thin sheet of plastic 52 such as polytetrafluoroethylene (Teflon, TM Dupont) as thermal barrier with a number of series connected thermocouples having their junctions positioned on alternate sides of the sheet. Typically the thermocouples are type K(chromel-alumel) though other thermocouples can be employed for special conditions or environments. The thermocouple elements are electrodeposited or applied as foils 40 and 42 on the two sides of the barrier 52 with junctions 48 and 50 positioned on opposite sides of barrier 52. Typically the ends of the thermocouples 44 and 46 are connected to copper leads 45 and 47 for connection to a potentiometer or other accurate millivolt measuring device. The thermal barrier 52 and attached thermocouples are encapsulated and calibrated so that a given voltage output from the thermopile translates into a precise value for the heat flow through the barrier when corrected for temperature related changes in thermocouple and barrier characteristics. Since the voltage outputs of the thermocouples are temperature dependant, a chart or algebraic relationship between temperature, observed output voltage and heat flux is required. This can be determined by test or provided by a manufacturer. In an alternate construction of the heat-flux sensor 22, nodes 48 and 50 are independent RTDs or thermocouples whose temperatures are independently observed and averaged for each side of the thermal barrier 52, whereby the heat flux through the barrier 52 can be calculated.

The emissivity of emitting surface 20 is calculated as follows: In the following sample calculation higher temperature 25 of heat source 24 is represented by T25. The lower temperature 31 of heat sink 30 is represented by T31. The voltage output of heat-flux sensor 22 is V23. The calibration constant of heat-flux sensor 22 is provided by the manufacturer as its sensitivity S in the reciprocal of (Watts/square meter) per microvolt (here V23). The heat flux through heat-flux sensor 22 in units of heat quantity per unit area or Q/A (heat flow divided by area in units such as Watts/square meter) is calculated from V23/S. This may be subject to a temperature dependant correction factor TCF provided by the heat-flux sensor manufacturer, frequently in the form of a power polynomial based on temperature where $TCF=BT^2+CT+D$ where B, C and D are constants also provided by the heat-flux sensor manufacturer. Therefore the heat-flux flowing through heat-flux sensor 22 is $Q/A=(V23 \times TCF)/S$. The observation of heat-flux requires that there be a temperature drop (change) across the heat-flux sensor. Knowing the thermal conductivity of the sensor and the heat quantity traversing it, the temperature drop can be calculated. Calculation of the temperature drop across the heat-flux sensor allows correction for the temperature drop to be applied to the observed temperature of heat source 24. The correction for temperature drop across the heat-flux sensor has been omitted from the following calculation.

Now, having heat flux Q/A and T25 and T31, only the Stephan-Boltzman constant is needed. This constant SB has different values, depending on the units selected. In units of Watts/square meter/$K^4$, where $K^4$ is the Absolute temperature on the Kelvin scale to the fourth power, SB is 5.67E-8 or 0.0000000567.

The emissivity of surface 20 is calculated using the equation $e=HF/SB(T25^4-T31^4)$ where all the constants and variables are in consistent units. While the temperatures T 25 and T31 may be reported in degrees Centigrade, the T25 and T31 in the equation are in degrees Kelvin or degrees Centigrade plus 273.

From the foregoing description, it can be seen that the present invention comprises an advanced measuring system for observing data from which direct measurement of emissivity or absorptivity of surfaces can be calculated. It will be appreciated by those skilled in the art that changes could be made to the embodiments described in the foregoing description without departing from the broad inventive concept thereof. It is understood, therefore, that this invention is not limited to the particular embodiment or embodiments disclosed, but is intended to cover all modifications and equivalents thereof which are within the scope and spirit of the invention as defined by the appended claims.

We claim:

1. An apparatus positionable in an environment having a known first temperature, for observing data for use in calculating emissivity of a radiating surface, said apparatus comprising:
   a heat source having a second temperature, said second temperature being higher than said first temperature;
   a temperature measurement device for determining the second temperature;
   a heat-flux sensor having a first side and a second side, said first side positioned in effective thermal contact with said heat source;
   a radiating surface positioned contiguous to and in substantial thermal contact with said second side of the heat-flux sensor; and
   whereby measurements from the temperature measurement device, the heat-flux sensor, and radiating surface determine the heat flow rate through the heat-flux sensor, and the heat flow rate through the heat-flux sensor and the first and second temperatures determine the emissivity of the radiating surface.

2. The apparatus as recited in claim 1, wherein a temperature of said radiating surface is substantially the same as said second temperature.

3. The apparatus as recited in claim 1 where the temperature of the radiating surface is inferable from the temperature determined by the temperature measurement device, the determined heat flow rate through the heat-flux sensor, and a thermal resistance of the heat-flux sensor.

4. The apparatus as recited in claim 1, where the heat source includes a heater for maintaining said heat source at said second temperature.

5. The apparatus as recited in claim 1 further comprising a container having a substantially cylindrical shape, a first end and a second end, said environment being maintained in said container and said radiating surface being disposed to face said second end.

6. The apparatus as recited in claim 5, wherein said second end has a conical shape.

7. The apparatus as recited in claim 5, wherein said container maintains a sub-atmospheric pressure environment therein.

8. The apparatus as recited in claim 7, wherein said sub-atmospheric pressure is a low pressure approximating $3E^{-11}$ bar.

9. A method for obtaining data for calculation of emissivity of a surface, comprising the steps of:
   a.) providing an environment of a known first temperature and a sub-atmospheric pressure;
   b.) providing a heat source within the environment;
   c.) providing a heat sink within the environment;
   d.) positioning one side of a heat flux sensor in heat exchange relation with the heat source within the environment;
   d.) positioning the surface in contiguous contact with an opposing side of the heat-flux sensor;
   e.) directing the surface toward the heat sink;
   f.) measuring a temperature of the heat source;
   g.) determining a rate of heat transmission through the heat-flux sensor;
   h.) determining a temperature of the heat sink; and,
   i.) calculating the emissivity of the surface using the measured temperature of the heat source, the determined temperature of the heat sink, and the determined rate of heat transmission through the heat-flux sensor.

10. The method as recited in claim 9, wherein the step of determining a rate of heat transmission through the heat-flux sensor includes the step of calculating a temperature drop across the heat flux sensor and subtracting the calculated temperature drop from the temperature of the heat source to thereby provide a more nearly correct value for a temperature of the surface.

11. A method for obtaining data for calculation of absorptivity of a surface, comprising the steps of:
   a.) providing an environment of a known first temperature and a sub-atmospheric pressure;
   b.) providing a heat source within the environment;
   c.) providing a heat sink within the environment;
   d.) positioning one side of a heat-flux sensor in heat exchange relation with the heat sink within the environment;
   e.) positioning the surface in contiguous contact with an opposing side of the heat-flux sensor;
   f.) directing the surface toward the heat source;
   g.) measuring a temperature of the heat source;
   h.) determining a rate of heat transmission through the heat-flux sensor;
   i.) determining a temperature of the heat sink; and, j.) calculating the absorptivity of the surface using the measured temperature of the heat source, the determined temperature of the heat sink, and the determined rate of heat transmission through the heat-flux sensor.

12. The method as recited in claim 11, wherein the step of determining a rate of heat transmission through the heat-flux sensor includes the step of calculating a temperature drop across the heat flux sensor and adding the calculated temperature drop to the temperature of the heat sink, to thereby provide a more nearly correct value for a temperature of the surface.

* * * * *